(12) United States Patent
Hribar et al.

(10) Patent No.: US 11,003,071 B2
(45) Date of Patent: May 11, 2021

(54) MASK FOR GENERATING FEATURES IN A MICROWELL PLATE

(71) Applicant: CYPRE, INC., San Francisco, CA (US)

(72) Inventors: Kolin Hribar, San Francisco, CA (US); Andrew Kelly, Boise, ID (US); Curtis Tom, San Mateo, CA (US)

(73) Assignee: CYPRE, INC., San Francisco, CA (US)

( * ) Notice: Subject to any disclaimer, the term of this patent is extended or adjusted under 35 U.S.C. 154(b) by 61 days.

(21) Appl. No.: 16/195,398

(22) Filed: Nov. 19, 2018

(65) Prior Publication Data

US 2019/0155146 A1     May 23, 2019

Related U.S. Application Data

(60) Provisional application No. 62/589,488, filed on Nov. 21, 2017.

(51) Int. Cl.
| | |
|---|---|
| *G01F 1/66* | (2006.01) |
| *G03F 1/66* | (2012.01) |
| *G03F 7/16* | (2006.01) |
| *C12M 1/12* | (2006.01) |
| *G03F 1/38* | (2012.01) |
| *C12M 1/32* | (2006.01) |
| *G03F 7/20* | (2006.01) |
| *C12M 1/00* | (2006.01) |

(Continued)

(52) U.S. Cl.
CPC ............. *G03F 1/66* (2013.01); *C12M 23/12* (2013.01); *C12M 23/20* (2013.01); *C12M 25/06* (2013.01); *G03F 1/38* (2013.01); *G03F 7/16* (2013.01); *G03F 7/2002* (2013.01); *G03F 7/0037* (2013.01); *G03F 7/038* (2013.01)

(58) Field of Classification Search
CPC .. C23C 16/00; G03F 9/00; G03F 7/20; C12Q 1/04; G01G 1/66; G01N 21/76
See application file for complete search history.

(56) References Cited

U.S. PATENT DOCUMENTS

| | | | |
|---|---|---|---|
| 5,912,095 A * | 6/1999 | Katakura | .......... G03F 1/22 378/35 |
| 6,057,163 A * | 5/2000 | McMillan | .......... G01N 21/6452 422/82.08 |
| 7,170,597 B1 | 1/2007 | Rushbrooke | |

(Continued)

FOREIGN PATENT DOCUMENTS

| | | | | |
|---|---|---|---|---|
| JP | 2013-156353 | * | 8/2013 | ............ G03F 7/20 |
| WO | 2015179572 | | 11/2015 | |

(Continued)

*Primary Examiner* — Dah-Wei D. Yuan
*Assistant Examiner* — Andrew J Bowman
(74) *Attorney, Agent, or Firm* — Fish IP Law, LLP

(57) ABSTRACT

Devices and methods for the manipulation and handling of light blocking masks suitable for controlled illumination of the wells of multi-well test plates are described. Such controlled illumination can be used to generate simple or complex three dimensional forms within the wells when used in combination with suitable photoactivatable polymer or gel precursors. Light blocking masks of the inventive concept can include features that stabilize or grip a multiwell plate when in use. Such masks can have apertures having a fixed configuration, or can have apertures with transient or changeable configurations.

5 Claims, 21 Drawing Sheets

(51) Int. Cl.
  *G03F 7/00* (2006.01)
  *G03F 7/038* (2006.01)

(56) References Cited

U.S. PATENT DOCUMENTS

| | | |
|---|---|---|
| 8,062,900 B2 | 11/2011 | Modavis |
| 2005/0169962 A1 | 8/2005 | Bhatia |
| 2006/0086321 A1* | 4/2006 | Brody .................. C23C 14/042 |
| | | 118/720 |
| 2013/0203146 A1 | 8/2013 | Ying |
| 2014/0093911 A1* | 4/2014 | Sun .................... G01N 33/5005 |
| | | 435/39 |
| 2016/0175800 A1 | 6/2016 | Murphy |
| 2017/0067025 A1 | 3/2017 | Nikkhah |
| 2017/0283766 A1* | 10/2017 | Hribar .................. B29C 64/135 |

FOREIGN PATENT DOCUMENTS

| | | | | |
|---|---|---|---|---|
| WO | 2016044483 | | 3/2016 | |
| WO | WO2017087693 | * | 5/2017 | ............ C12M 23/12 |

* cited by examiner

MASK FOR GENERATING FEATURES IN A MICROWELL PLATE

This application claims the benefit of U.S. Provisional Application Ser. No. 62/589,488 filed on Nov. 21, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is light-blocking masks, particularly light-blocking masks utilized in photopolymerization.

BACKGROUND

The background description includes information that may be useful in understanding the present invention. It is not an admission that any of the information provided herein is prior art or relevant to the presently claimed invention, or that any publication specifically or implicitly referenced is prior art.

There is growing interest in the fabrication of three dimensional matrices for use in in vitro cultivation of cells, as such cultivated cells more closely mimic the response of tissues and organs of living organisms. Such in vitro cultivation of cells is typically carried out in the wells of a multi-well plate. Unfortunately, generation of suitable three dimensional matrices within the confines of such wells poses significant technical challenges.

Many approaches to generating complex three dimensional matrices utilize photopolymerizable pre-polymers or photoactivatable gel precursors, in combination with devices to control light entering the well. For example, International Patent Application Publication No. WO 2015/179572 (To Chung et al.) describes the use of a digital micromirror device to focus light through the open top and onto discrete areas of individual wells in order to affect controlled polymerization of a photopolymerizable prepolymer. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Such an approach, however, is hampered by the inevitable presence of bubbles on at the liquid/air interface. In addition, it is not apparent that such an approach is scalable.

United States Patent Application Publication No. 2016/0,175,800 discusses a method in which cylindrical forms or molds are inserted into the wells that contain a photoactivatable gel precursor, which are then illuminated from below to cause formation of a gel within the well. Withdrawal of the form leaves a cylindrical pillar in the center of the well. As such the forms that can be generated within the well are limited to those provided on available molds, and are not readily customizable. While illumination is performed through a photomask, it is not apparent that this does more than block cross-illumination between wells.

Various light blocking masks for use with microwell plates have been proposed. For example, U.S. Pat. No. 7,170,597 (to Rushbrooke and Hooper) describes the use of a mask having 96 openings that correspond in position to the wells of a 96-well microwell plate. These opening serve to limit light used to illuminate the microwell plate for analytical purposes to the test wells of the plate. Similarly, U.S. Pat. No. 8,062,900 (to Modavis) describes the use of a similar static light blocking mask to limit the area of illumination provided to a microwell plate having wells that include optical waveguide gratings used for analytical purposes. Such light blocking masks, however, are limited to providing a single and unchanging region of illumination within a well.

In another approach, U.S. Pat. No. 6,057,163 (to McMillan) describes the use of a sliding mask that overlays a microwell plate used for assays that incorporate photoluminescence. The mask includes openings for a portion of the wells of the microwell plate, blocking light emitted from the test wells that immediately surround a well being characterized and reducing crosstalk between test wells. In order to permit utilization of the entire test plate the mask slides over the surface of the plate, exposing different sets of wells as it moves. This approach, however, significantly impacts the time required to expose all the wells of a microwell plate.

International Patent Application No. WO 2016/044483 (to Hribar et al.) discusses using a series of photomasks that, when applied in series in combination with suitable illumination, can generate well-type structures on planar surfaces from photopolymerizable prepolymers. As described in U.S. patent application Ser. No. 15/645,979 (to Hribar et al), three dimensional matrices can be produced within the wells of a microwell plate using photopolymerization processes. As described in this application a variety of three dimensional features can be generated using one or more light blocking masks placed between a light source providing a polymerization-inducing wavelength (e.g. UV) and the underside of a microwell plate. Openings of various sizes and configurations in the light-blocking mask control the passage of polymerization-inducing light into the wells and provide controlled polymerization of discrete regions within the wells. Handling and control of such light blocking masks, however, is not addressed.

Thus, there is still a need for a device that provides efficient and effective generation of three dimensional features in the wells of a microwell plate.

BRIEF DESCRIPTION OF THE DRAWINGS

FIG. 6A depicts a first photomask having a hexagonal aperture positioned between a light source and the bottom of well. FIG. 6B depicts the well of FIG. 6A containing a photopolymerizable hydrogel precursor, which is being illuminated through the hexagonal aperture by the light source. FIG. 6C depicts the well of FIG. 6B following polymerization and removal of excess hydrogel precursor, and shows the deposition of a hexagonal hydrogel solid on the bottom of the well. FIG. 6D depicts the well of FIG. 6C, in which a second photomask having a round aperture is interposed between the bottom of the well and the light source. FIG. 6E depicts the well of FIG. 6D, in which a second photopolymerizable hydrogel precursor has been added to the well and in which the well is illuminated through the round aperture. FIG. 6F depicts the well of FIG. 6E following polymerization and removal of the second hydrogel precursor, and shows deposition of a cylindrical hydrogel solid on the previously deposited hexagonal hydrogel solid.

FIG. 7A depicts a first photomask having a round aperture positioned between a light source and the bottom of well. FIG. 7B depicts the well of FIG. 7A containing a first photopolymerizable hydrogel precursor, which is being illuminated through the round aperture by the light source. FIG. 7C depicts the well of FIG. 7B following polymerization and removal of excess first hydrogel precursor, and shows the deposition of a cylindrical hydrogel solid on the bottom of the well. FIG. 7D depicts the well of FIG. 7C, in which a second photomask having a toroidal aperture is interposed between the bottom of the well and the light source. FIG. 7E depicts the well of FIG. 7D, in which a second photopolymerizable hydrogel precursor has been added to the well and in which the well is illuminated through the toroidal aperture. FIG. 7F depicts the well of FIG. 7E following polymerization and removal of the second hydrogel precursor, and shows deposition of a hollow cylindrical hydrogel solid on the periphery of the previously deposited cylindrical hydrogel solid. FIG. 7G shows the well of FIG. 7F following instillation of a volume of cells in suspension within the open cavity formed by combined hydrogel solids. Such cells can be suspended in a high density or high viscosity liquid, or in a polymerizable hydrogel precursor. FIG. 7H depicts the well of FIG. 7G, in which a third photomask having a round aperture is interposed between the bottom of the well and the light source. FIG. 7I depicts the well of FIG. 7H, in which a third photopolymerizable hydrogel precursor has been added to the well and in which the well is illuminated through the round aperture of the third photomask. The third photopolymerizable hydrogel precursor can have a density and/or viscosity that prevents mixing with the cell suspension during the polymerization period. FIG. 7J depicts the well of FIG. 7I following polymerization and removal of the third hydrogel precursor, and shows deposition of a hollow cylindrical hydrogel solid on the previously deposited hollow cylindrical hydrogel solid, thereby encapsulating the cell suspension within hydrogel solid generated in situ.

DETAILED DESCRIPTION

Figure 1:
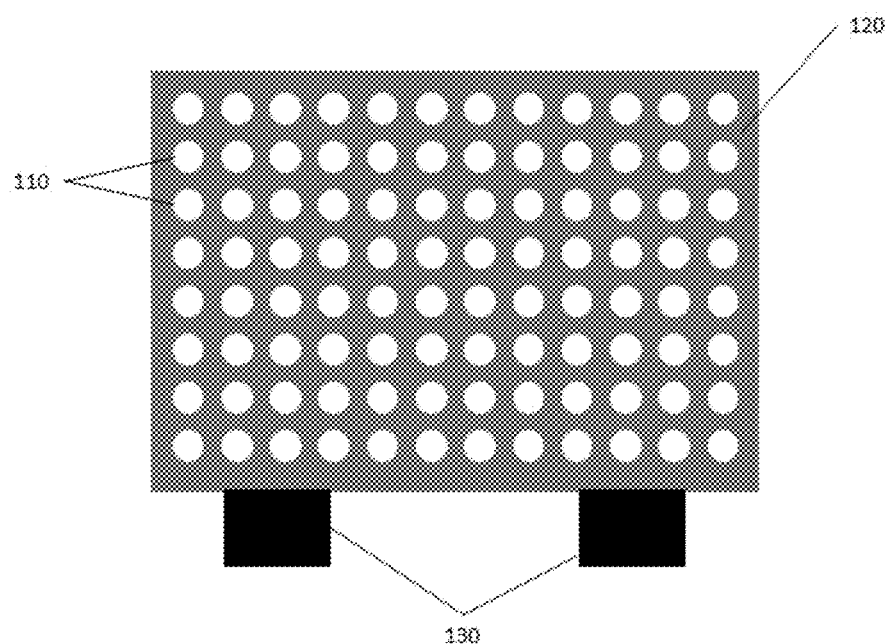
FIG. 1 depicts an embodiment of the inventive light blocking mask configured for use with a 96-well microwell plate, with a pair of handling features.

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems and methods in which one or more light blocking masks provided with manipulative tabs are provided. Such a light blocking mask can include two or more apertures. In some embodiments an aperture can be a through hole in the material of the light blocking mask. In other embodiments an aperture can include or be composed of a material that is at least partially transmissive (e.g. exhibiting about 5%, 10%, 20%, 30%, 40%, 50%, 60% 70%, 80%, 90%, or more than 90% transmittance) to the wavelength selected for fabrication. Such transmittance can be fixed (e.g. as a result of application of a partially opaque coating) or variable. Variable transmittance through an aperture can be provided through the use of electrooptical materials, use of liquid crystal technology in combination with a polarizing filter, or other suitable techniques.

At least a portion of such an aperture corresponds to at least one well of a microwell plate and permits the passage of light into at least a portion of the well when positioned between a light source and the underside of the microwell plate. These apertures can be provided in any suitable shape or size, and provide an illumination profile corresponding to at least a portion of a three dimensional feature that is to be generated within the interior of the illuminated well. Suitable light blocking masks are dimensioned to permit them to be readily installed in and removed from a printing device that includes a light source and platform for supporting a microwell plate, without the use of tools. To facilitate this suitable light blocking masks can include various additional features. Such additional features include one or more low friction regions corresponding to contact points with the printing device and alignment features (e.g. indents, slots, through holes, etc.) that interact with features of the printing device to ensure proper alignment during illumination.

The light blocking portions of the mask can be made of any material suitable to block, absorb, or otherwise prevent or reduce the transmission of the selected wavelength through such portions of the mask. For example, if an ultraviolet wavelength is utilized for fabrication of structures within the wells of a microwell plate the light blocking portions of the mask can be made of a material that absorbs or reflects UV wavelengths. In some embodiments light blocking portions of the mask (or portions thereof) can block essentially all (i.e. >95%) transmission of the selected wavelength through such portions. In other embodiments light blocking portions of the mask (or portions thereof) can block part (e.g. about 10%, 20%, 30%, 40%, 50%, 60%, 70%, 80%, 90%, or more) of the selected wavelength through such a portion. This can be accomplished by, for example, providing a partial coating of a light absorbing and/or reflective substance on a base material that transmits light. Suitable light blocking materials include polymers (e.g. polypropylene, polystyrene, polycarbonate, nylon, etc.), metals (such as aluminum, stainless steel, etc.), glass (such as borosilicate glass), and/or a mineral (such as quartz, sapphire, etc.). In some embodiments the base material of the light blocking mask can be transmissive the selected wavelength but coated with a material that at least partially blocks transmission of the selected wavelength. For example, a light blocking mask made primarily of a transmissive polymer or quartz can have a non-transmissive metal (e.g. aluminum, chromium, etc.) film applied to areas where light blocking is desired. Alternatively, active materials such as electrooptical materials or liquid crystal/polarizer assemblies can be used to provide similarly partial or complete blocking of light through a light transmitting base material.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Various objects, features, aspects and advantages of the inventive subject matter will become more apparent from the following detailed description of preferred embodiments, along with the accompanying drawing figures in which like numerals represent like components.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Devices and methods of the inventive concept can employ one or more light blocking masks, which serve to control the intensity and/or configuration of light being directed into one or more wells of a multi-well test plate. Light passing through the mask can be used to trigger polymerization or gelation of precursor polymers or gels, resulting in the formation of polymer or gel solids within a well so exposed. The conformation of such solids is a function of the conformation of an aperture in the mask through which the light passes on its way to the well. Such an aperture can be fixed or non-transient aperture, having a single conformation resulting from its construction. Such fixed or non-transient apertures can be, for example, a through-hole in the mask or a transparent or a portion of the mask that is at least partially transparent to wavelengths used for photoactivation of polymerization or gelation. Such fixed or non-transient apertures can have a variety of shapes (e.g. circular, elliptical, polygonal, irregular, etc.). It should be appreciated, however, that such fixed or non-transient apertures can provide considerable variety by using two or more masks having fixed or non-transient apertures in combination. For example, a series of masks with different fixed or non-transient apertures can be used in succession to expose different portions of the well to light from the light source. Alternatively, two or more masks with differently configured fixed or non-transient apertures can be used in combination (for example, by aligning their respective apertures to permit the passage of light).

Alternatively, a mask of the inventive concept can have one or more transient or changeable apertures. Such transient or changeable apertures can change their configuration, for example by using optically active materials that permit localized control of the passage of light through that portion of the mask. For example, a portion of a mask positioned beneath a well of a multiwell plate can include a liquid crystal panel and a polarizing filter that permit light capable of initiating polymerization or gelation to pass through when the plane of polarization of the liquid crystal panel is approximately parallel with that of the polarizing filter. Rotating the plane of polarization of the liquid crystal panel (for example by energizing or de-energizing the liquid crystal panel) can result in blocking the passage of light to the well. A transient or changeable aperture can include a plurality of such liquid crystal panel, selective energizing of which permits a single region of the mask corresponding to a well of the multiwell plate to provide a transient or changeable aperture capable of having a plurality of configurations. Such selective energizing can be provided using a controller, which can include a database of different aperture configurations and a user interface. In such embodiments a single mask having such transient or changeable apertures can provide a wide variety of aperture configurations, permitting the generation of a wide variety of conformations for solids produced on the test surface.

In some embodiments of the inventive concept a mask can include a device for holding or stabilizing the multiwell plate against a surface of the mask. Such device can actively grip or press against a surface of the multiwell plate, for example through the use of a clamp, spring, piston, or similar device that presses itself against the plate surface so as to hold it in place relative to the mask. In some embodiments the mask can include a channel, depression, cavity, or similar indentation that conforms to a portion of the surface of the multiwell plate, such that the multiwell plate held in place and stabilized passively during use. In some embodiments a mask of the inventive concept includes both active gripping and passive stabilization features.

Figure 2:
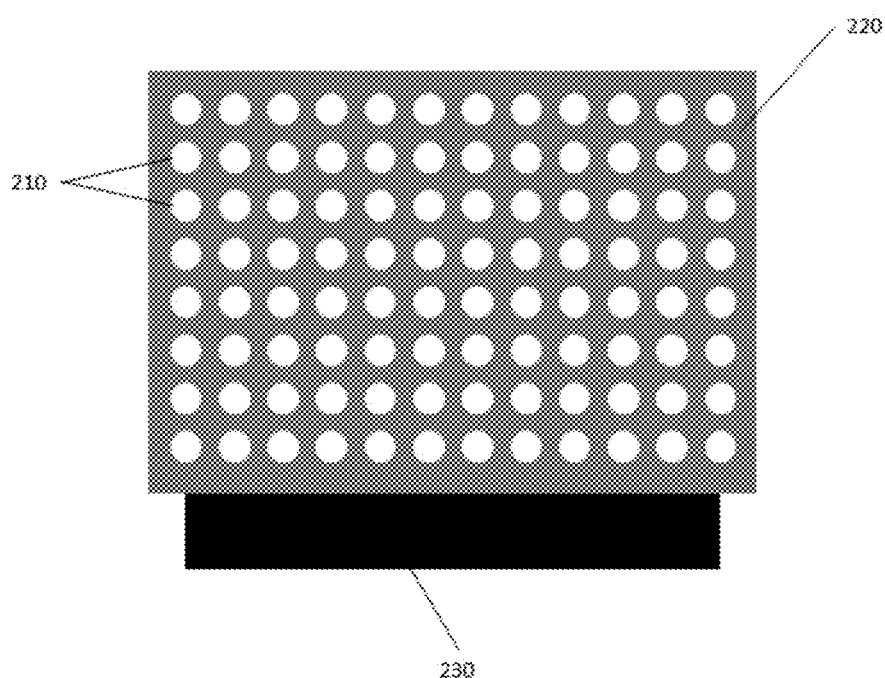
FIG. 2 depicts an embodiment of the inventive light blocking mask configured for use with a 96-well microwell plate, with a single handling feature.

As noted above, a light blocking mask of the inventive concept can include one or more handling features dimensioned to facilitate gripping by hand. Such handling features can be coupled to the periphery of the mask, for example to an edge that is does not come into direct contact with a printer utilizing the mask when in use. Examples of such handling features are shown in FIG. 1 and FIG. 2. FIG. 1 shows an example of a light blocking mask of the inventive concept having apertures 110 and a light blocking portion 120. As shown, this implementation has a pair of handling features 130 extending from the periphery of the mask. FIG. 2 shows a similar embodiment of a light blocking mask having apertures 210 and a light blocking region 220. As shown, a single handling feature 230 extends from the periphery of the mask.

Figure 3:
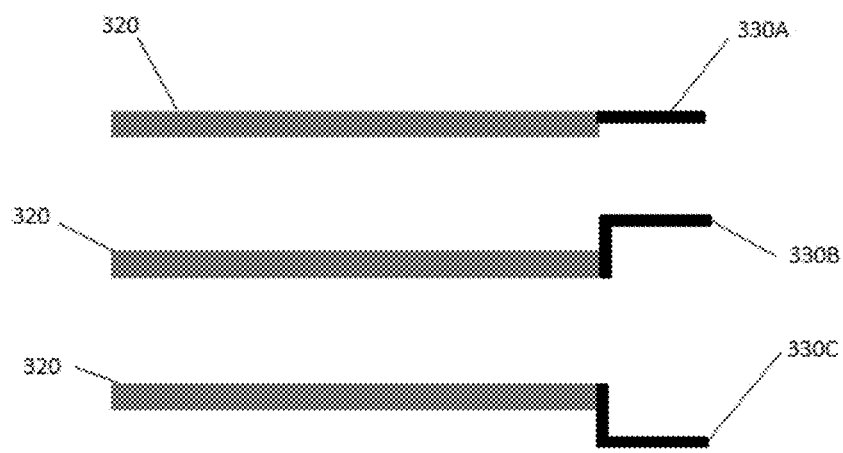
FIG. 3 depicts three embodiments of the inventive light blocking mask showing handling features in different planes, coplanar with the light blocking portion (top), above the light blocking portion (middle), and below the light blocking portion (bottom).

As shown in FIG. 3, such handling features can extend from an edge of the light blocking mask in different planes relative to the plane defined by the light blocking mask. As shown in the top portion of FIG. 3, a handling feature 330A can extend within the same or essentially the same plane as that of the light blocking mask 320. FIG. 3 also depicts embodiments in which a handling feature extends into a plane above 330B or below 330C the plane of the light blocking mask 320. It should be appreciated that such placement can facilitate handling of light blocking masks when two or more masks are arranged together for use in combination.

Although such handling features are described above as projections from the light blocking mask, a handling feature can be an indent or notch (such as a semicircular, triangular, or square notch) directed centrally from the periphery of the light blocking mask. Such handling features can be formed as part of the light blocking mask, or formed separately and coupled to the main body of the light blocking mask in a subsequent step. Such coupling can be performed by any suitable means, including welding, adhesives, and mechanical fasteners. In some embodiments the handling features are permanently attached. In other embodiments the handling features are readily (i.e. without the use of tools) removable, or can be detached and re-attached as desired by a user.

In some embodiments of the inventive concept the light blocking portion of the light blocking mask is provided as a removable insert or tray, which lies within a frame that supports the handling features. Such an insert or tray can be held in place on the frame by a friction fit between the insert or tray and one or more corresponding surfaces of the frame. Alternatively, an insert or tray can include one or more features (such as a through hole, notch, and/or indentation) that interacts with a corresponding mating feature (such as a spring loaded pin or projection) on the frame. In still other embodiments the insert or tray can be held in place by a mechanical coupling, such as hook and loop closure, clip, or clamp. In still other embodiments the insert or tray can be held in place by an adhesive. Such an adhesive can be a tacky adhesive that permits repeated removal and replacement of the insert or tray in a frame or a series of frames.

As noted above, light blocking masks of the inventive concept can be used in conjunction with a printing device. In use the light blocking mask can be positioned between a light source of the printing device and the underside of a microwell plate in which printing of three dimensional structures is to take place. Light blocking masks of the inventive concept can include features to facilitate this use.

Figure 4:
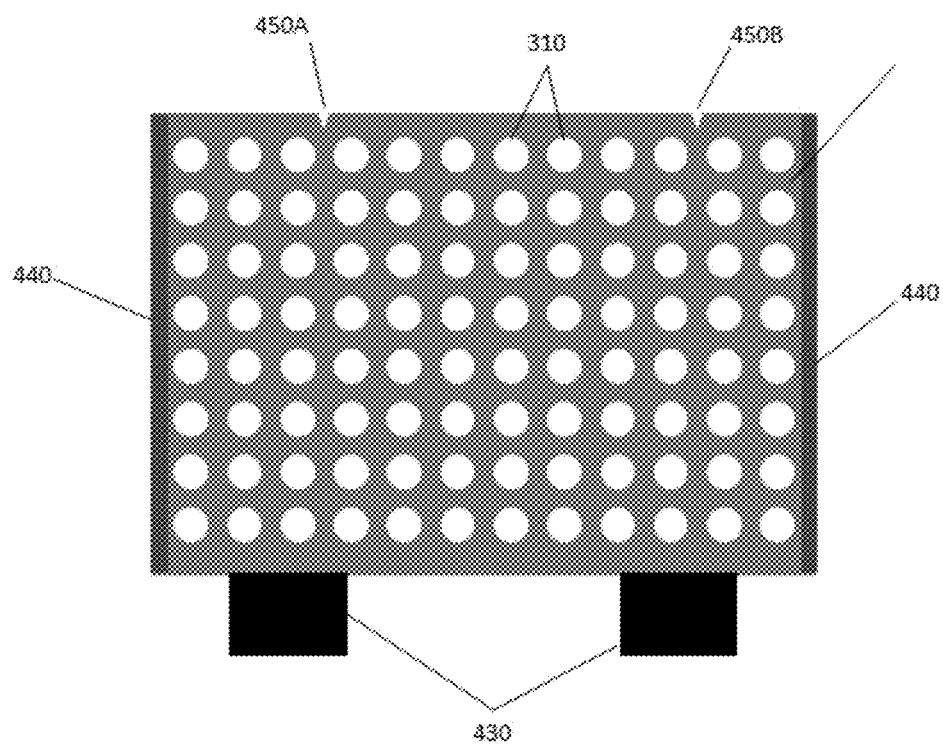
FIG. 4 depicts an embodiment of the inventive light blocking mask of the inventive concept with low friction regions and alignment features.

As shown in FIG. 4, light blocking masks of the inventive concept can include one or more regions that include a low friction material 440, such as a low friction polymer (e.g. polypropylene, Teflon, etc.) or polymer coating. Such low friction regions can be positioned along the periphery of the light blocking mask and/or in other areas that are likely to come into contact with the printing device on insertion and removal of the mask. Such low friction regions simplify use and reduce wear of the light blocking mask.

Also shown in FIG. 4, some embodiments of light blocking masks of the inventive concept can include alignment features 450A, 450B that interact with complementary alignment features of the printing device when in use. Such alignment features can be distributed asymmetrically to define orientation of the light blocking mask. For example, alignment feature 450A is positioned more centrally along a long axis of the light blocking portion 420 of the light blocking mask that alignment feature 450B. As a result in order interact properly with complementary alignment features on an associated printer (e.g. pins or protuberances that fit within alignment notches on correct insertion) the light blocking mask must be inserted in the proper orientation. Positioning of the handling features 430 in the appropriate plane relative to the light blocking region 420 can also aid in proper orientation.

Alignment features of the printing device can be dedicated alignment features (e.g. spring loaded pins, indentations, projections, etc.) and/or structural features of the printing device. For example, a light blocking mask of the inventive concept can include a through-hole that permits passage of a spring-loaded pin of the printing device when the light blocking mask is properly inserted. The pin can subsequently be withdrawn to permit removal of the mask. Alternatively, a light blocking mask of the inventive concept can include an indentation that aligns with and permits insertion of a projection of the printing device when the mask is properly positioned.

In some embodiments a light blocking mask of the inventive concept can include human and/or machine-readable indicia that identify the light blocking mask. Such identification can indicate the number of openings in the mask, their shape, their size, their distribution, the microwell plates that they are compatible with, etc. Suitable machine-readable indicia include a barcode, a QR code, and RFID chips (either active or passive).

Figure 5:
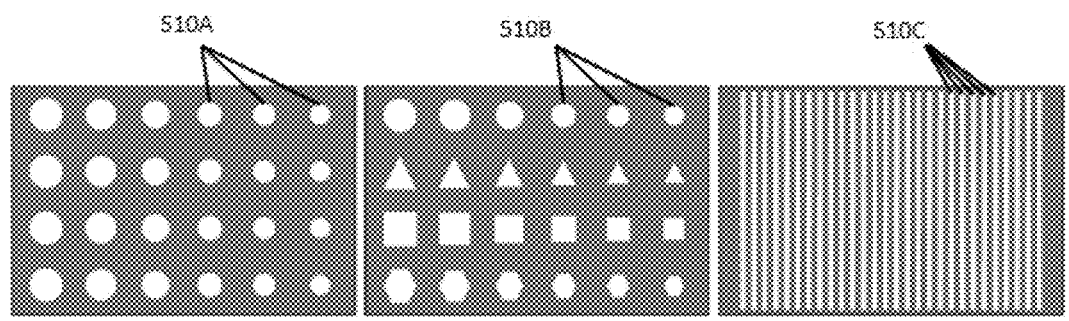
FIG. 5 depicts three embodiments of the inventive light blocking masks with different aperture sizes, shapes, and arrangements.

It should be appreciated that the apertures provided with light blocking masks of the inventive concept can have any suitable shape or dimension. A single light blocking mask can have identical apertures or include apertures of various configurations. FIG. 5 depicts light blocking masks with apertures of various shape, size, and/or configuration. The leftmost mask of FIG. 5 has apertures (510A) that are all circular but that vary in diameter across the mask. The central mask of FIG. 5 has apertures (510B) of different shapes (i.e. circular, triangular, square, and hexagonal) that vary in size across the mask. In some embodiments a single aperture is associated with a single well of a microwell plate when in use. In other embodiments a single aperture can span across multiple wells of a microwell plate when in use. The rightmost mask of FIG. 5 includes a set of linear apertures 510C each of which extends across the light blocking region and interacts with more than one well when utilized with a multiwell plate. Apertures can be round, elliptical, semi-circular, square, rectangular, hexagonal, polygonal, or asymmetrical. Similarly, apertures can be dimensioned and positioned such that from 5% to 100% of the floor of a microwell plate is illuminated when the light blocking mask is in use. In some embodiments the degree of light transmission through the apertures can vary across a light blocking mask, for example through partial coating with a light blocking substance or through use of dynamically adjustable opacity as described above.

In some embodiments light blocking masks of the inventive concept are provided as a set of individual masks. In such a set each member can have a different arrangement, size, and/or shape of apertures that permit the transmission of the selected wavelength. Such a set of light-blocking masks can be used in series to generate complex three dimensional features within the wells of a microwell plate. Alternatively, two or more light-blocking masks can be aligned with each other and utilized simultaneously to provide a composite aperture having a shape or size not provided by an individual mask. In such a set the handling features can be staggered or otherwise offset in order to facilitate selective removal and/or replacement of one or more light-blocking masks from the set.

In use, such a light blocking mask can be utilized with a printing device that includes a light source emitting the desired wavelength and a support for a microwell plate. A light blocking mask is placed between the light source and the underside of the microwell plate, with at least some of the apertures of the light blocking mask aligning with one or more wells of the microwell plate. For example, a slot can be provided in the printing device that is dimensioned and positioned to accommodate a light blocking mask in close proximity or contact with the underside of a microwell plate on the support. The light blocking mask can be inserted by manually grasping a handling feature and sliding the mask into the slot until it is appropriately positioned and/or aligned. This process can be facilitated through the use of alignment features as described above. Such alignment features can provide tactile feedback to a user indicating when the proper position has been achieved. In some embodiments proper positioning can be indicated by an alert (for example, a tone or light) provided by the printing device.

Figure 6A:
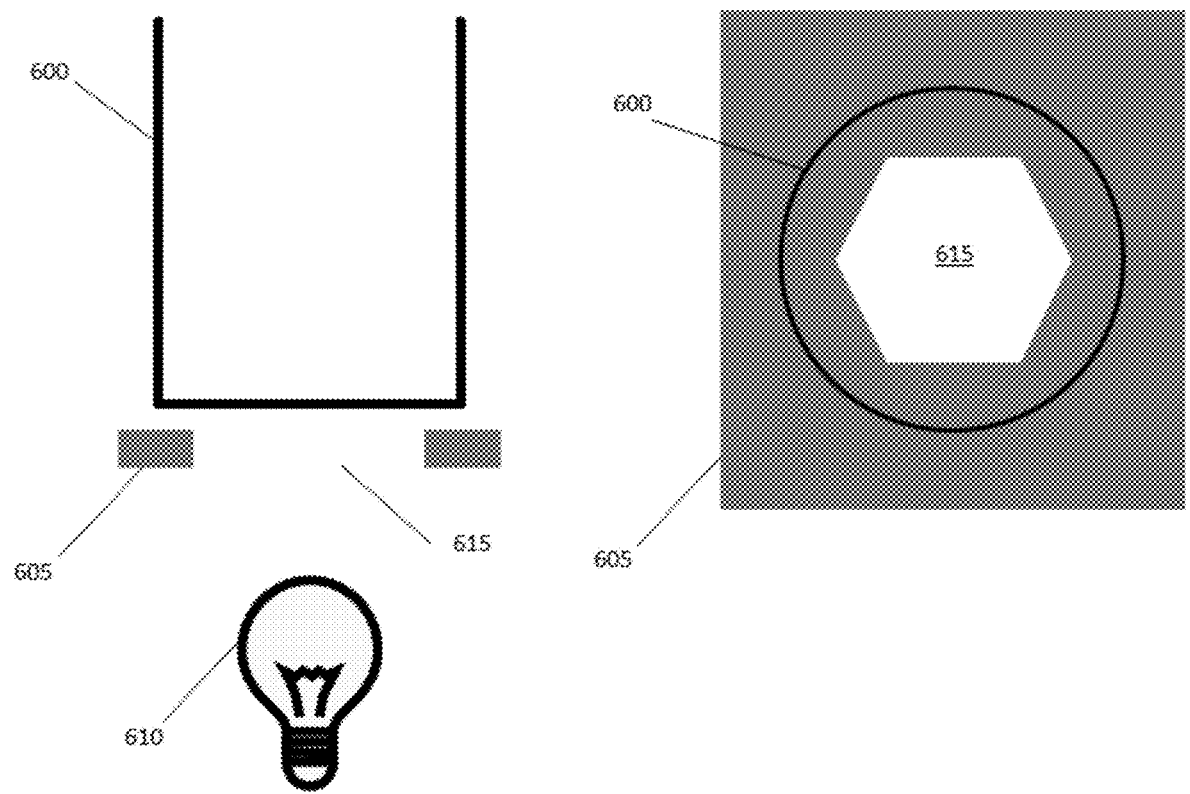
FIGS. 6A to 6F depict an exemplary method of the inventive concept for production of a three dimensional hydrogel solid within a well of a multiwell plate. Cross sections of side views are shown in the left panels. Top-down views are shown in the right panels.
Figure 6B:
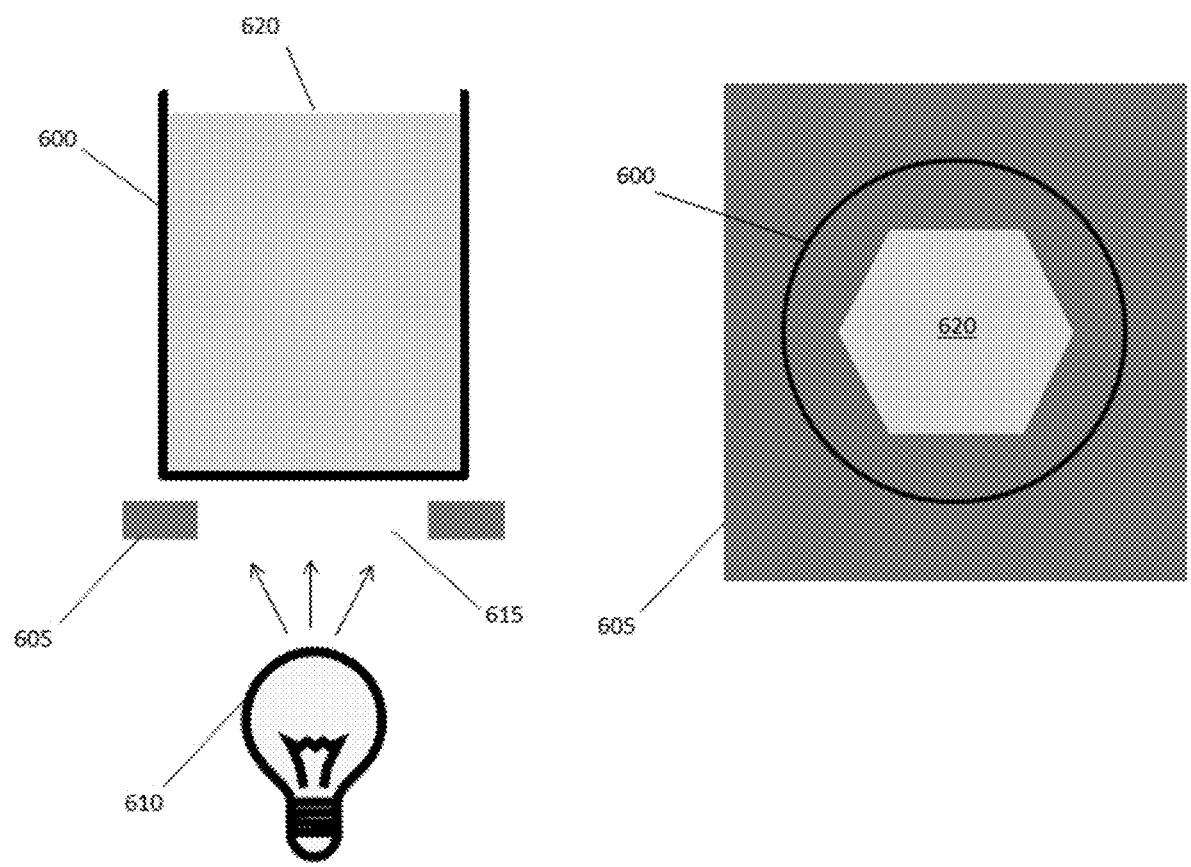
Figure 6C:
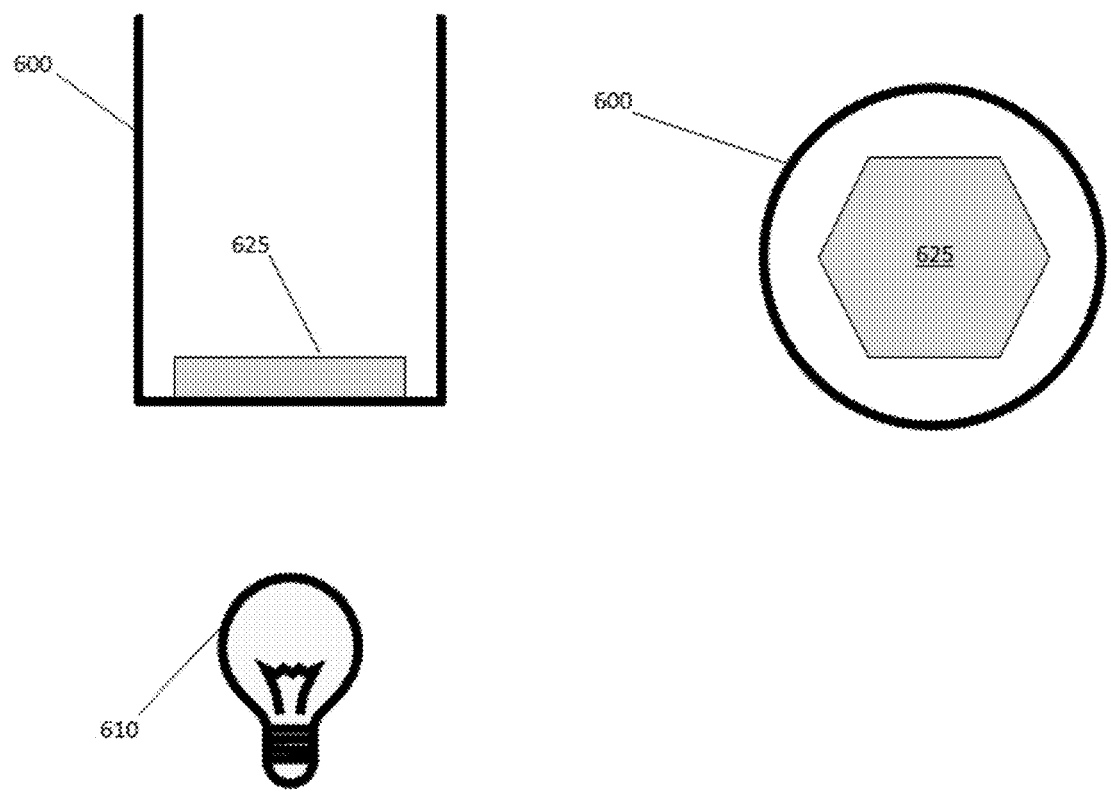

Other embodiments of the inventive concept include methods for generating complex, three dimensional hydrogel forms on a surface (e.g. the floor of a well of a microwell plate) using one or more light blocking masks as described above. An example of such an embodiment is shown in FIGS. 6A to 6F. In these figures a cross sectional view from the side is provided in the left panel, while a top-down view through the open top of a test well is provided in the right panel. FIG. 6A shows a test well 600 and a light source 610 with a light blocking mask 605 interposed between them. In this example the light blocking mask includes a hexagonal aperture 615 that is approximately centrally aligned with the well. FIG. 6B depicts the well 600 of FIG. 6A to which a photopolymerizable hydrogel precursor 620 has been added. At this step the light source 610 can be powered on, resulting in illumination of the well through aperture 615 of the photomask. Such illumination causes photopolymerization that generates a solid or semisolid hydrogel from the photopolymerizable hydrogel precursor. FIG. 6C depicts the well 600 following a period of illumination sufficient to generate a first hydrogel solid 625 on the floor of the well and rinsing/washing to remove unreacted photopolymerizable hydrogel precursor. As shown, the conformation of the first hydrogel solid 625 reflects the shape of the aperture 615 of the light blocking mask 605 (as shown in FIG. 6A).

Figure 6D:
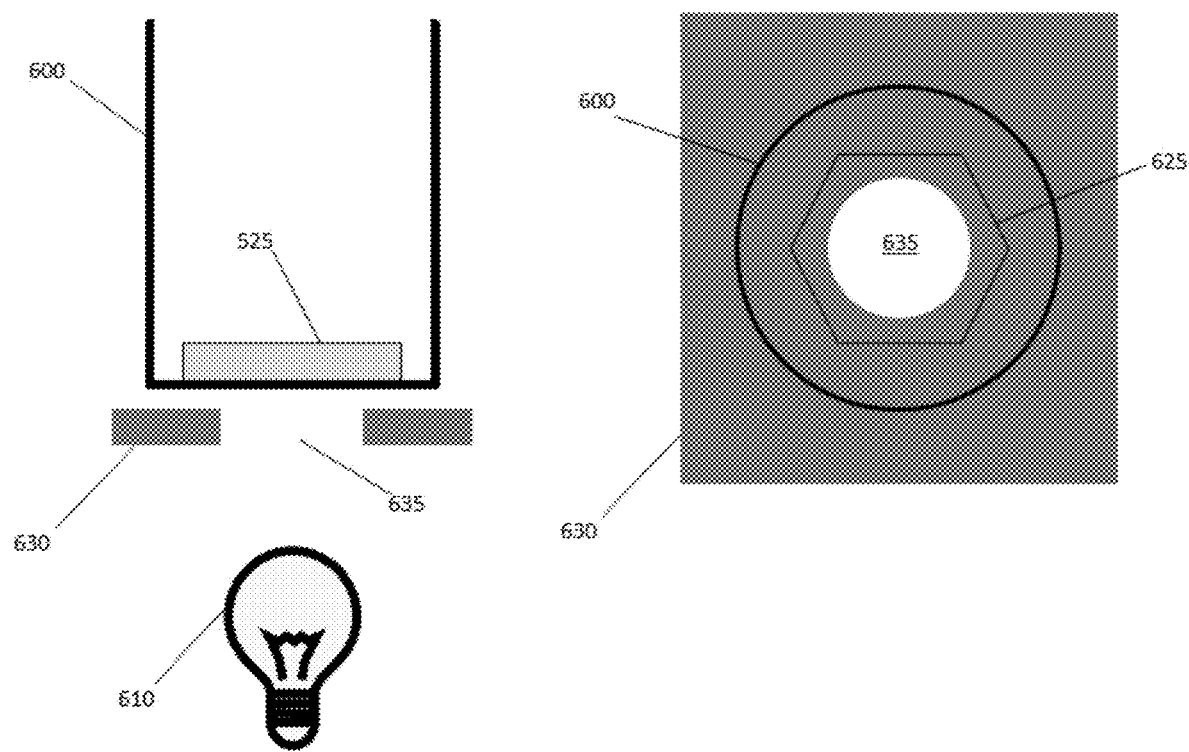
Figure 6E:
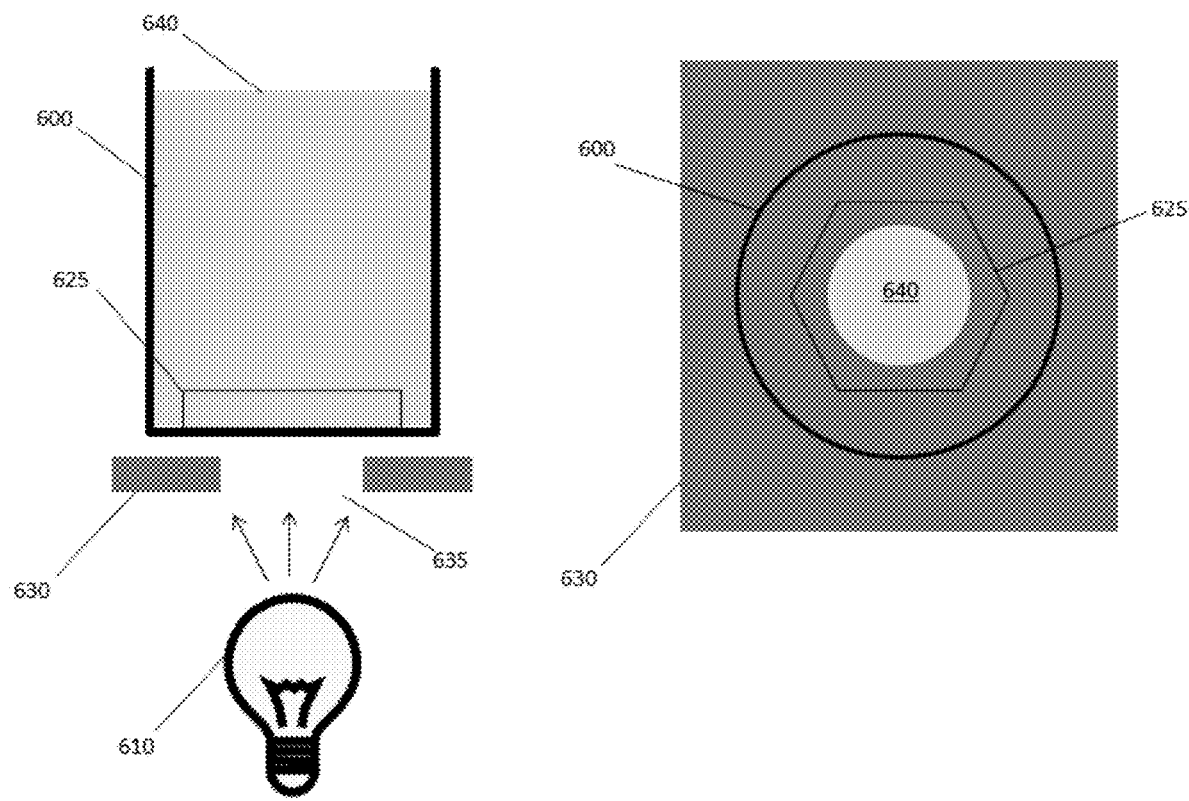
Figure 6F:
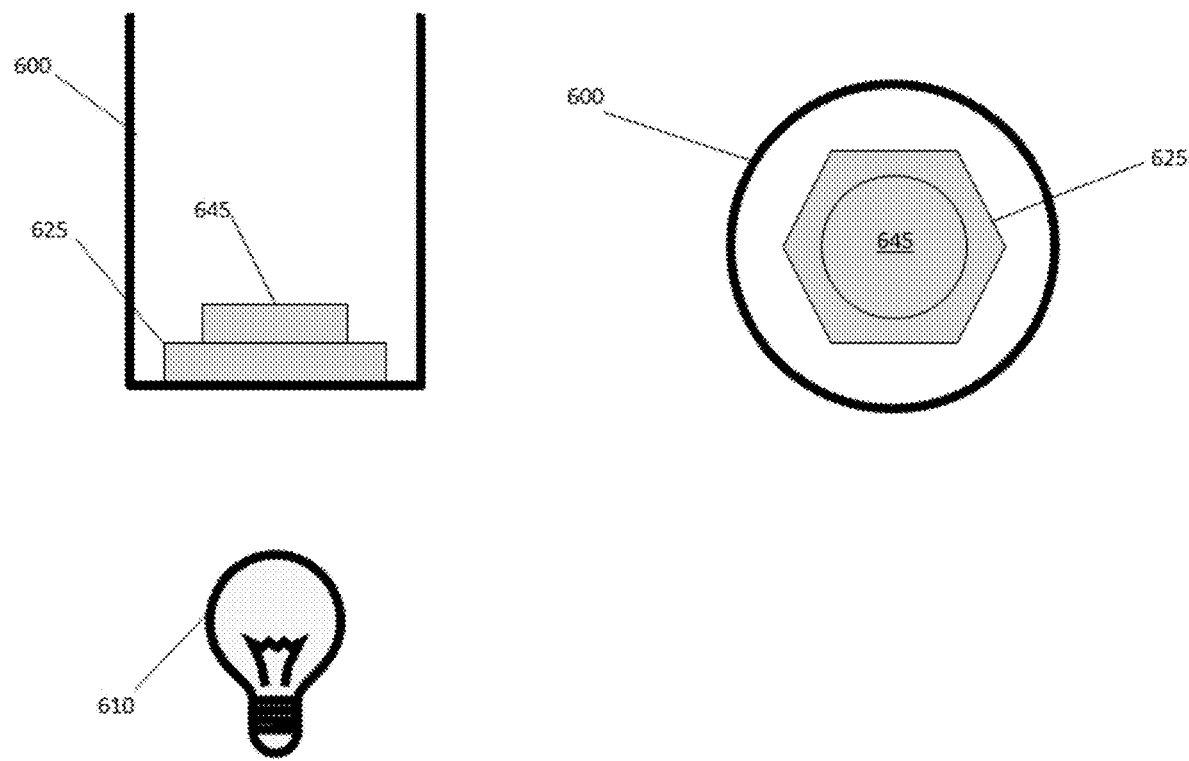

This process can be continued in order to generate more complex three dimensional hydrogel forms within the well by changing the light blocking mask and repeating the process. As shown in FIG. 6D, a different light blocking mask 630 has been interposed between the well 600 and the light source 610. If a light blocking mask with transient apertures is used this can be achieved by changing the configuration of the aperture, for example by using a controller as described above. The aperture 635 of this mask is circular, and also positioned essentially concentrically with the well 600. It should be appreciated, however, that an aperture can be positioned to illuminate any suitable portion of such a well, for example by providing a light blocking photomask in which the aperture is so positioned when the photomask is aligned with the microwell plate or by adjusting the position of the light blocking photomask relative to the microwell plate. In FIG. 6E a second photopolymerizable hydrogel precursor 640 has been added to the well 600 and the light source 610 powered on to provide illumination of the well through the aperture 635 of the light blocking photomask 630. The second photopolymerizable hydrogel precursor can be the same as or different from the first photopolymerizable hydrogel precursor, which permits variation in hydrogel composition and/or physical properties across the three dimensional hydrogel form generated within the well. After illumination for a suitable period of time a composite hydrogel form that includes a hexagonal hydrogel form 625 coupled to the bottom of the well 600 and a cylindrical hydrogel form 645 coupled to the hexagonal hydrogel form is generated, which is revealed by rinsing/washing to remove unreacted second photopolymerizable hydrogel precursor (as shown in FIG. 6F).

Although FIGS. 6A to 6F depict the generation of a two-part hydrogel form within the well, it should be appreciated that more complex forms can be generated by repeating the process and replacing and/or repositioning the light blocking photomask. It should also be appreciated that, while the depicted exemplary method includes removal of unreacted photopolymerizable hydrogel precursor between illumination steps, such removal is not necessary if the composition of the resulting hydrogel form is intended to be consistent throughout. In addition, light blocking photomasks having different degrees of transmissiveness can be used in series to generate forms with varying hydrogel densities across the final form.

Figure 7A:
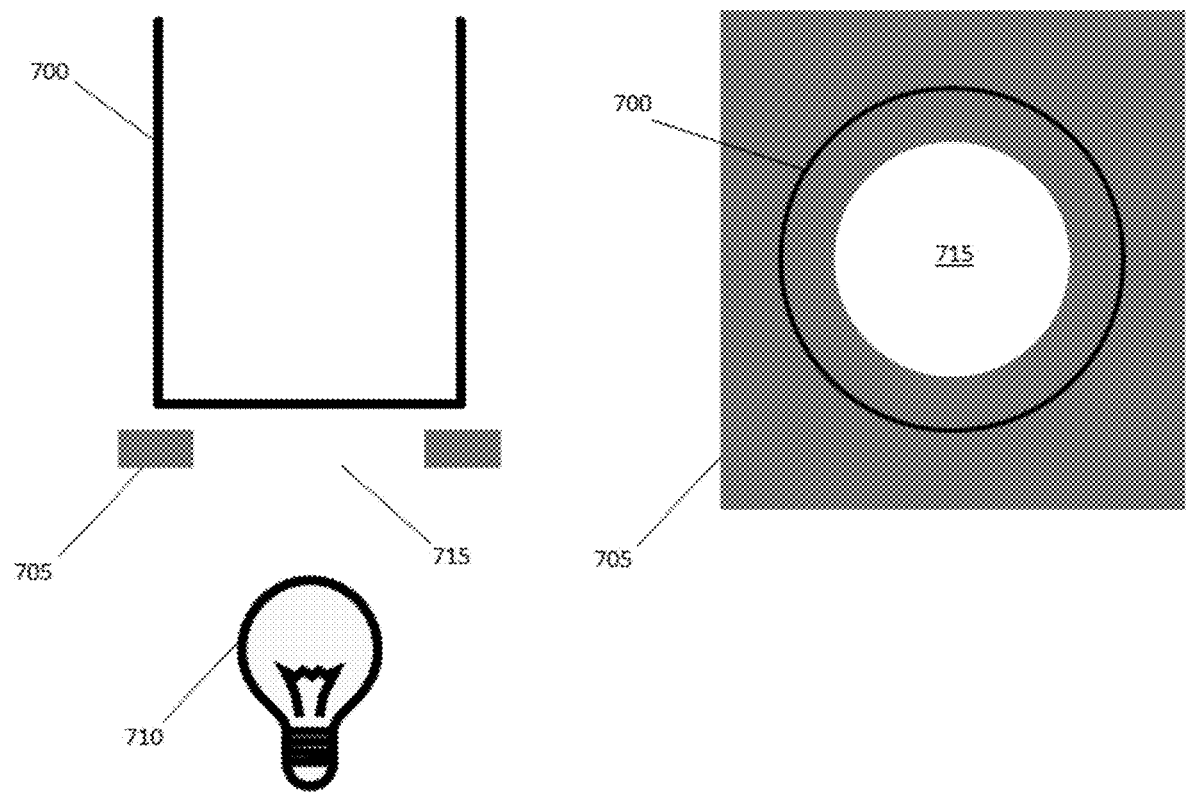
FIGS. 7A to 7J depict an exemplary method of the inventive concept for production of a three dimensional hydrogel solid within a well of a multiwell plate, where the solid has a hollow interior that encapsulates a suspension of cells. Cross sections of side views are shown in the left panels. Top-down views are shown in the right panels.
Figure 7B:
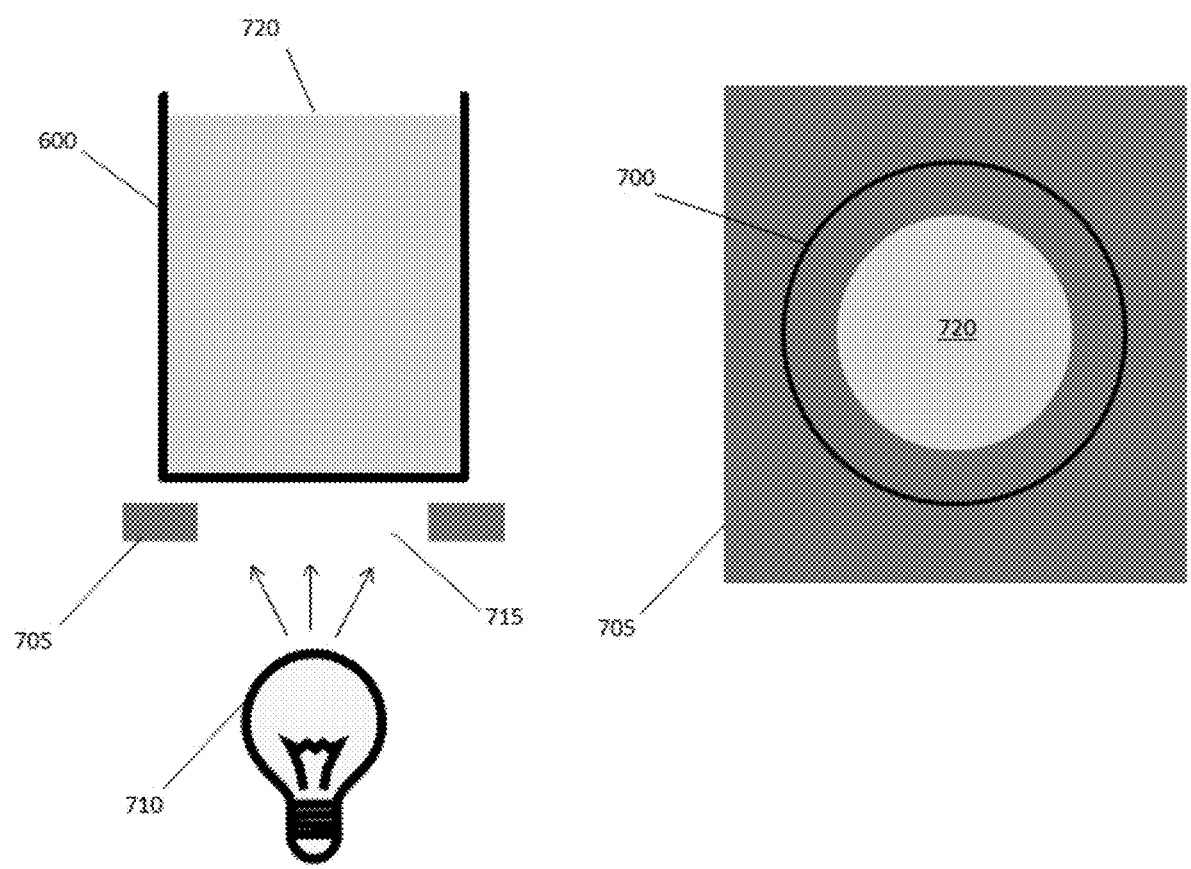
Figure 7C:
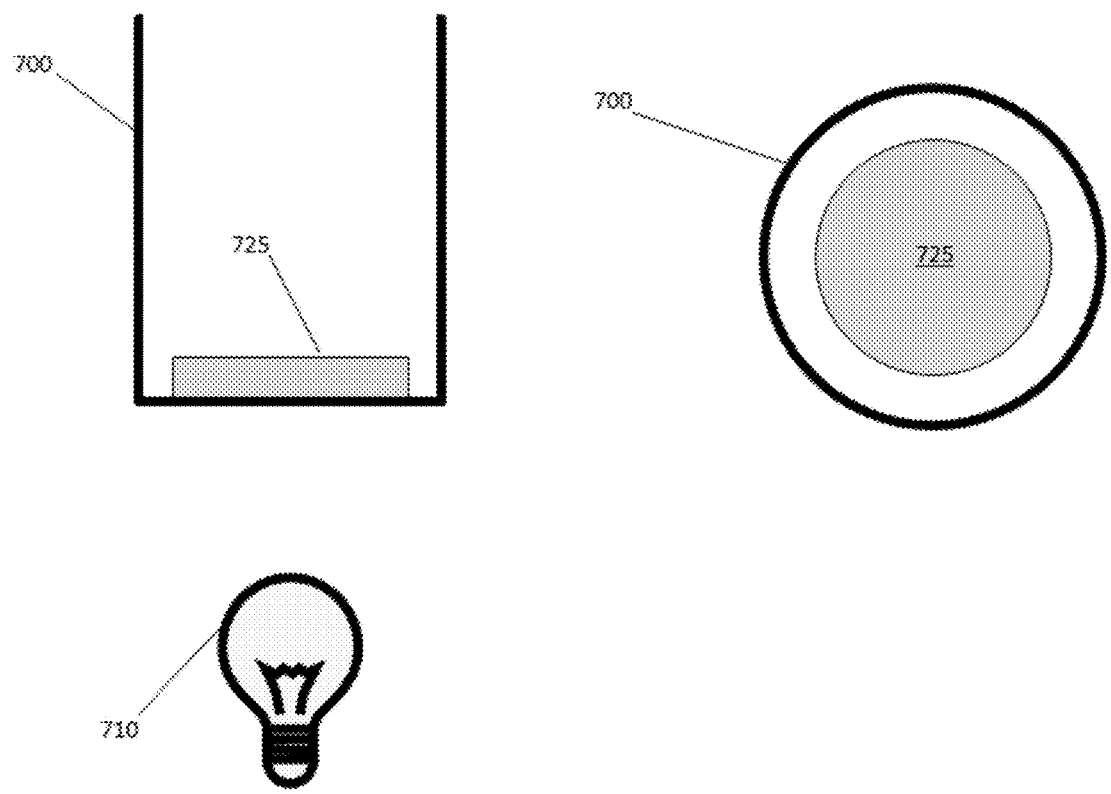

Another example of a method of the inventive concept is depicted in FIGS. 7A to 7J, which provide for encapsulating or enclosing a population of cells within a hydrogel form having an interior void. Such encapsulated cells can advantageously be kept in culture in a common environment with other cells within the well while avoiding direct contact between the encapsulated and non-encapsulated cells. In these figures a cross sectional view from the side is provided in the left panel, while a top-down view through the open top of a test well is provided in the right panel. FIG. 7A shows a test well 700 and a light source 710 with a light blocking mask 705 interposed between them. In this example the light blocking mask includes a circular aperture 715 that is approximately centrally aligned with the well. FIG. 7B depicts the well 700 of FIG. 7A to which a photopolymerizable hydrogel precursor 720 has been added. At this step the light source 710 can be powered on, resulting in illumination of the well through aperture 715 of the photomask. Such illumination causes photopolymerization that generates a solid or semisolid hydrogel from the photopolymerizable hydrogel precursor. FIG. 7C depicts the well 700 following a period of illumination sufficient to generate a first hydrogel solid 725 on the floor of the well and rinsing/washing to remove unreacted photopolymerizable hydrogel precursor. As shown, the conformation of the first hydrogel solid 725 reflects the shape of the aperture 715 of the light blocking mask 705 (as shown in FIG. 7A).

Figure 7D:
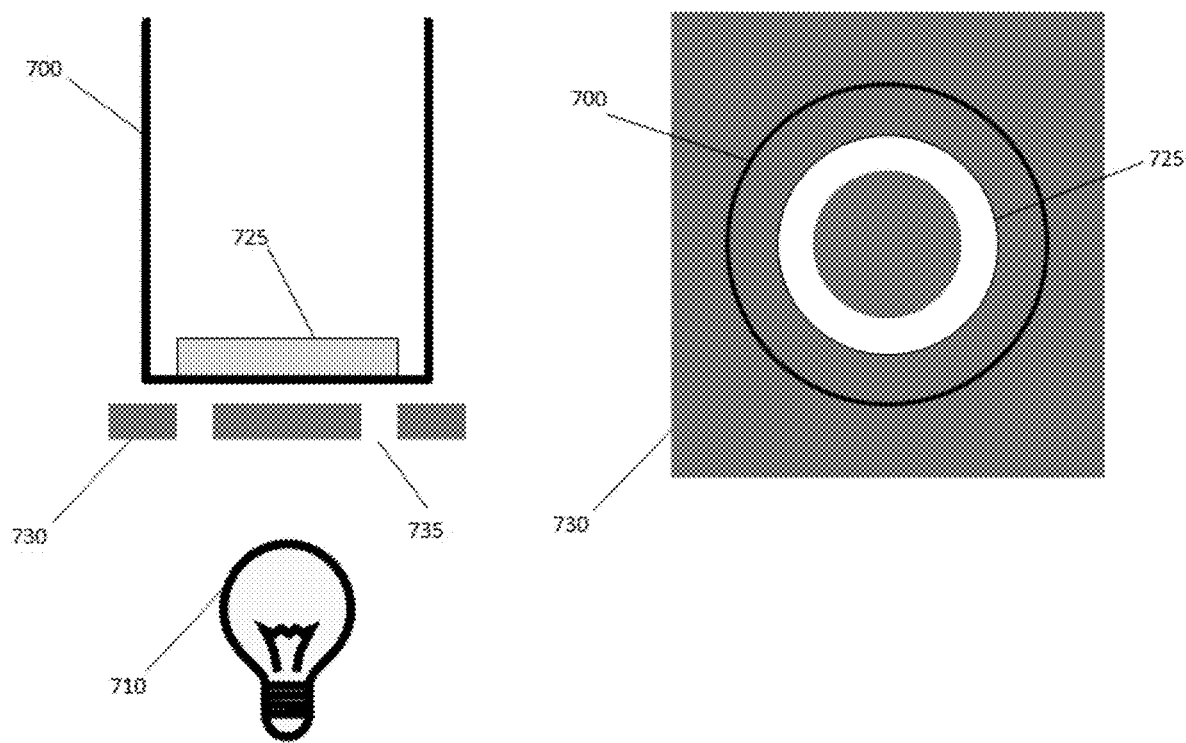
Figure 7E:
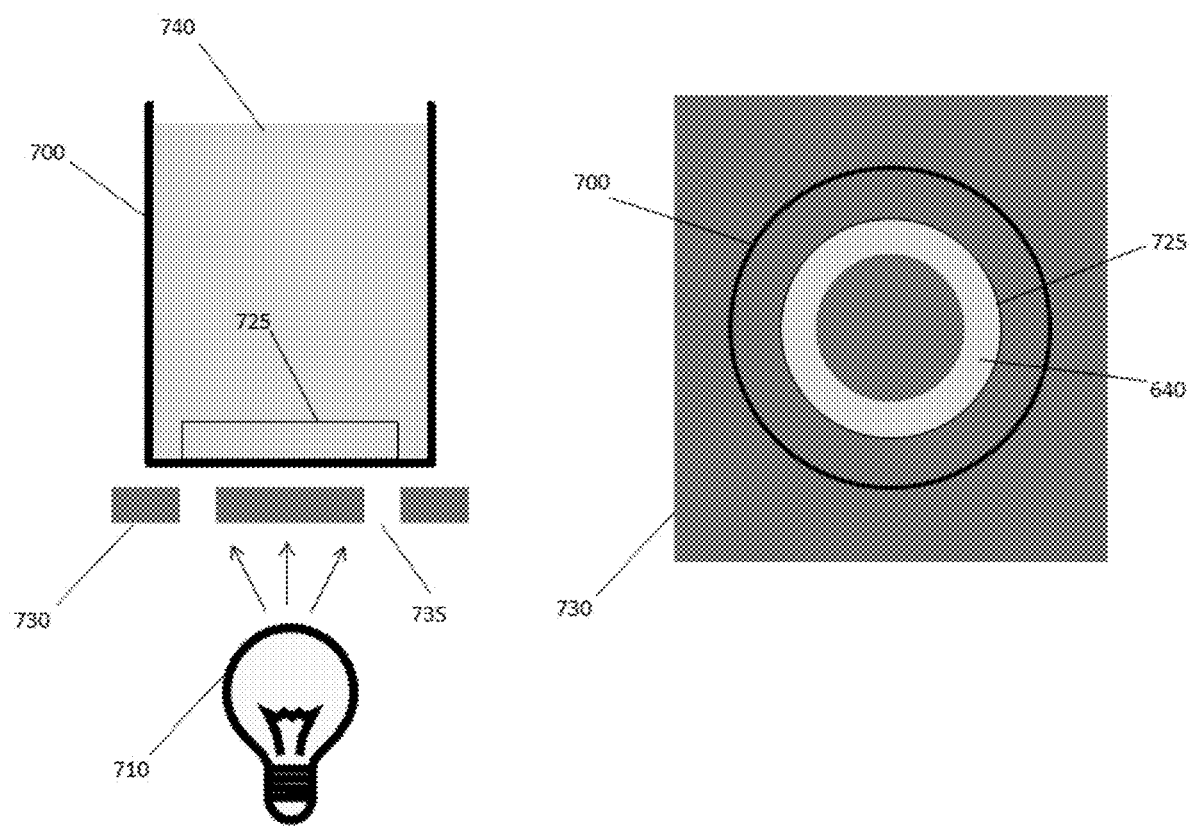

This process can be continued in order to generate side walls of the encapsulating hydrogel form by changing the light blocking mask and repeating the process. As shown in FIG. 7D, a different light blocking mask 730 has been interposed between the well 700 and the light source 710. If a light blocking mask with transient apertures is used this can be achieved by changing the configuration of the aperture, for example by using a controller as described above. The aperture 735 of this mask is ring, and is also positioned essentially concentrically with the well 700 and the first hydrogel solid. It should be appreciated, however, that an aperture can be positioned to illuminate any suitable portion of such a well, for example by providing a light blocking photomask in which the aperture is so positioned when the photomask is aligned with the microwell plate or by adjusting the position of the light blocking photomask relative to the microwell plate. In FIG. 7E a second photopolymerizable hydrogel precursor 740 has been added to the well 700 and the light source 710 powered on to provide illumination of the well through the aperture 735 of the light blocking photomask 730. The second photopolymerizable hydrogel precursor can be the same as or different from the first photopolymerizable hydrogel precursor, which permits variation in hydrogel composition and/or physical properties across the three dimensional hydrogel form generated within the well. After illumination for a suitable period of time an intermediate composite hydrogel form that includes the cylindrical hydrogel form 725 coupled to the bottom of the well 700 and a open cylinder hydrogel form 745 coupled to the cylindrical hydrogel form is generated, which is revealed by rinsing/washing to remove unreacted second photopolymerizable hydrogel precursor (as shown in FIG. 7F).

Figure 7F:
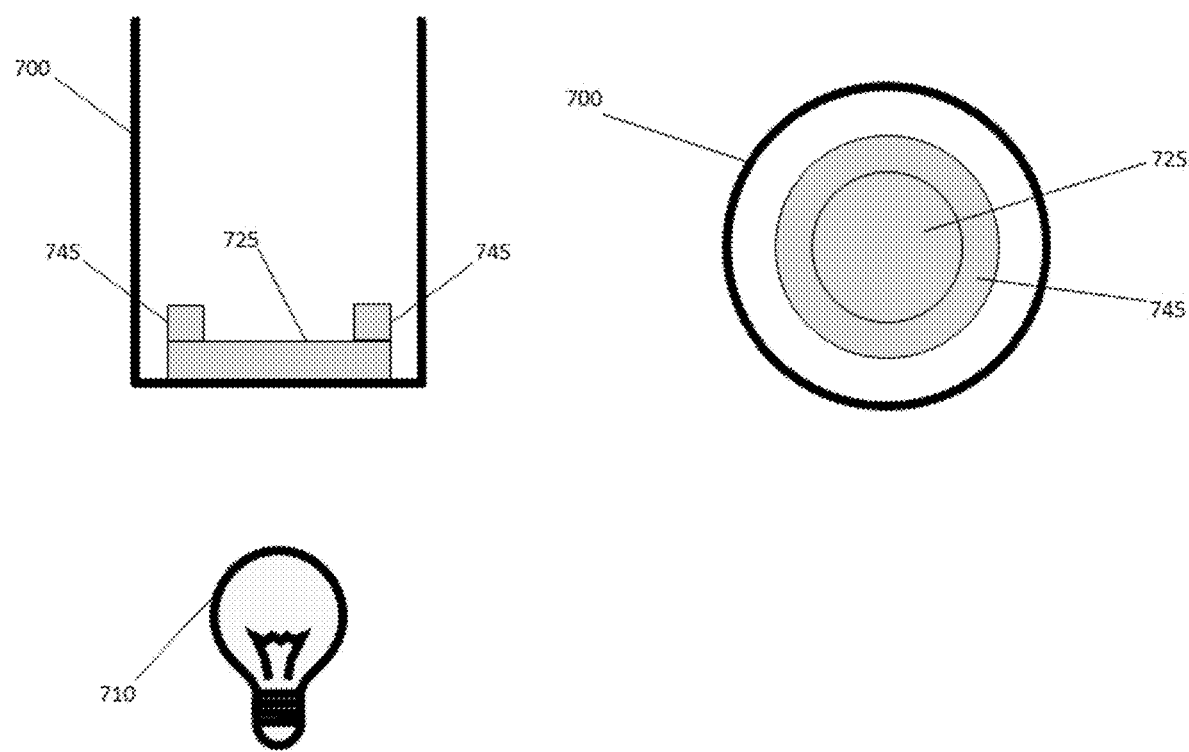
Figure 7G:
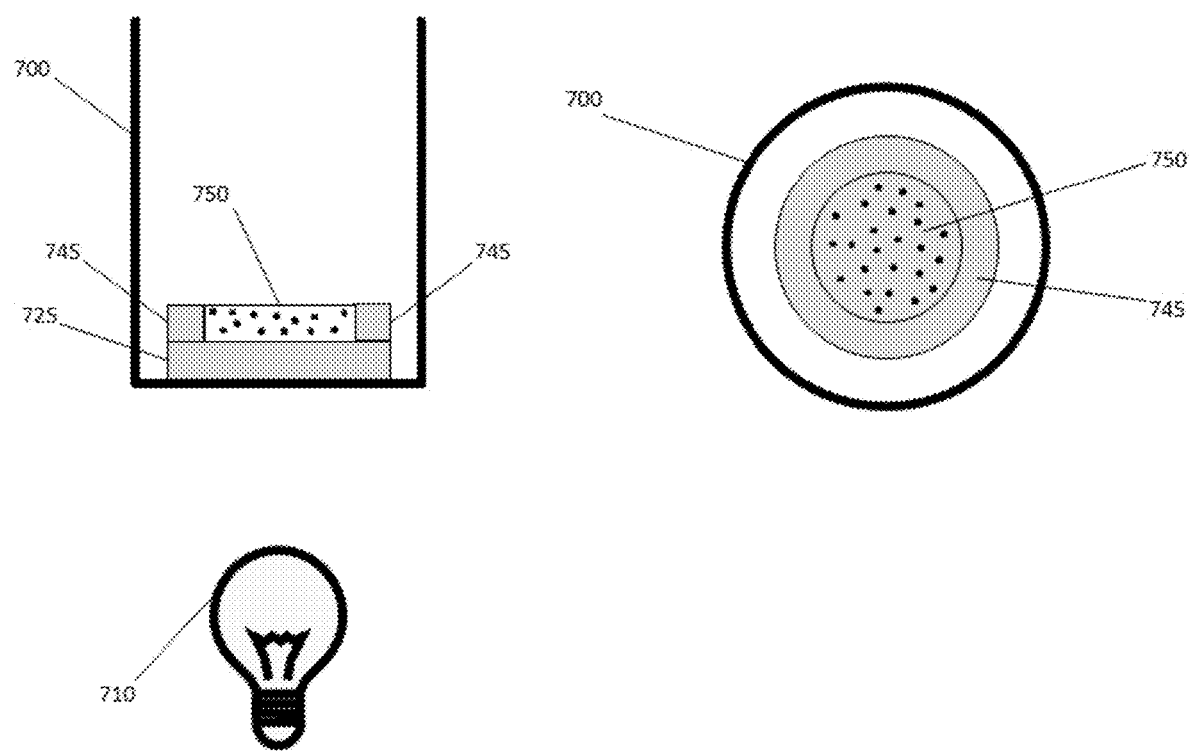

As shown in FIG. 7F, the intermediate composite hydrogel form includes an open pocket with a hydrogel floor and wall. FIG. 7G depicts a step in which a suspension of cells 750 has been instilled within the pocket formed by the joined cylindrical 725 and open cylinder 745 hydrogel forms. This suspension of cells can be provided in a media that has a relatively high density (e.g. greater than 1.1 g/cm$^3$) or viscosity that reduces or prevents mixing with liquids provided in subsequent steps. For example, elevated density can be provided by adding a non-ionic, low molecular weight compound (e.g. sucrose) to the media used to suspend the cells. In turn this low molecular weight compound can diffuse through the hydrogel layer following enclosure/encapsulation of the cells to provide more typical media conditions.

Figure 7H:
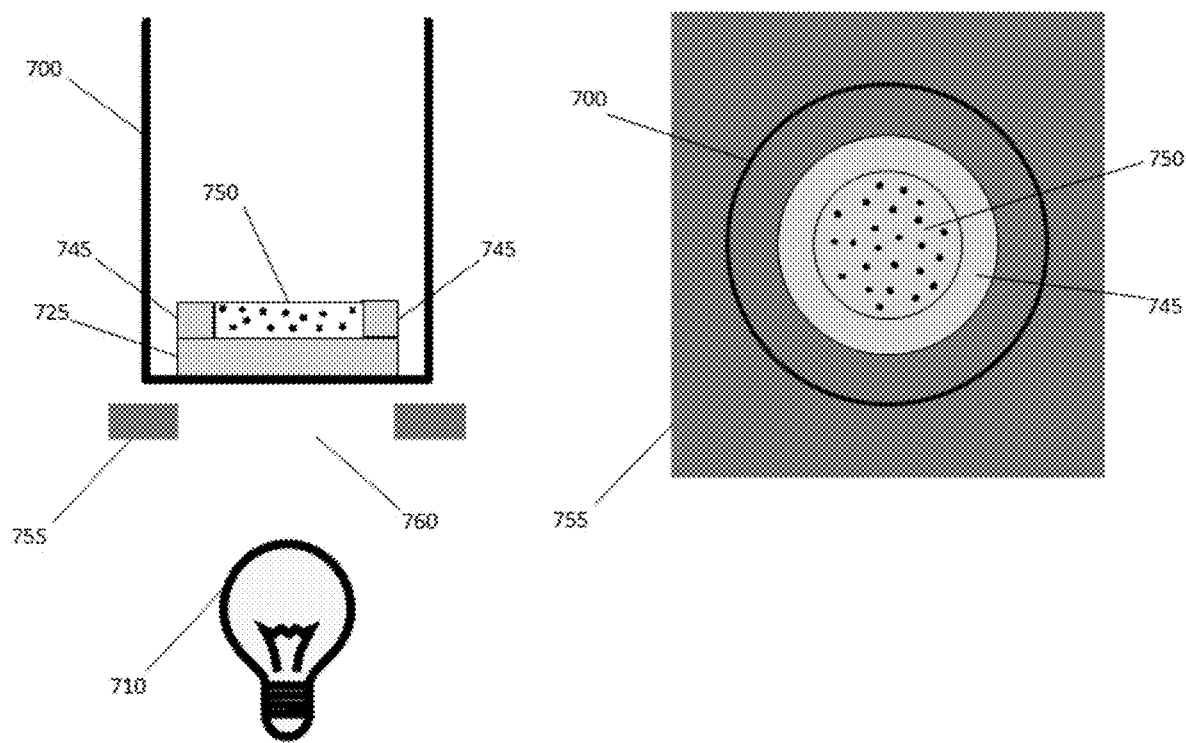
Figure 7I:
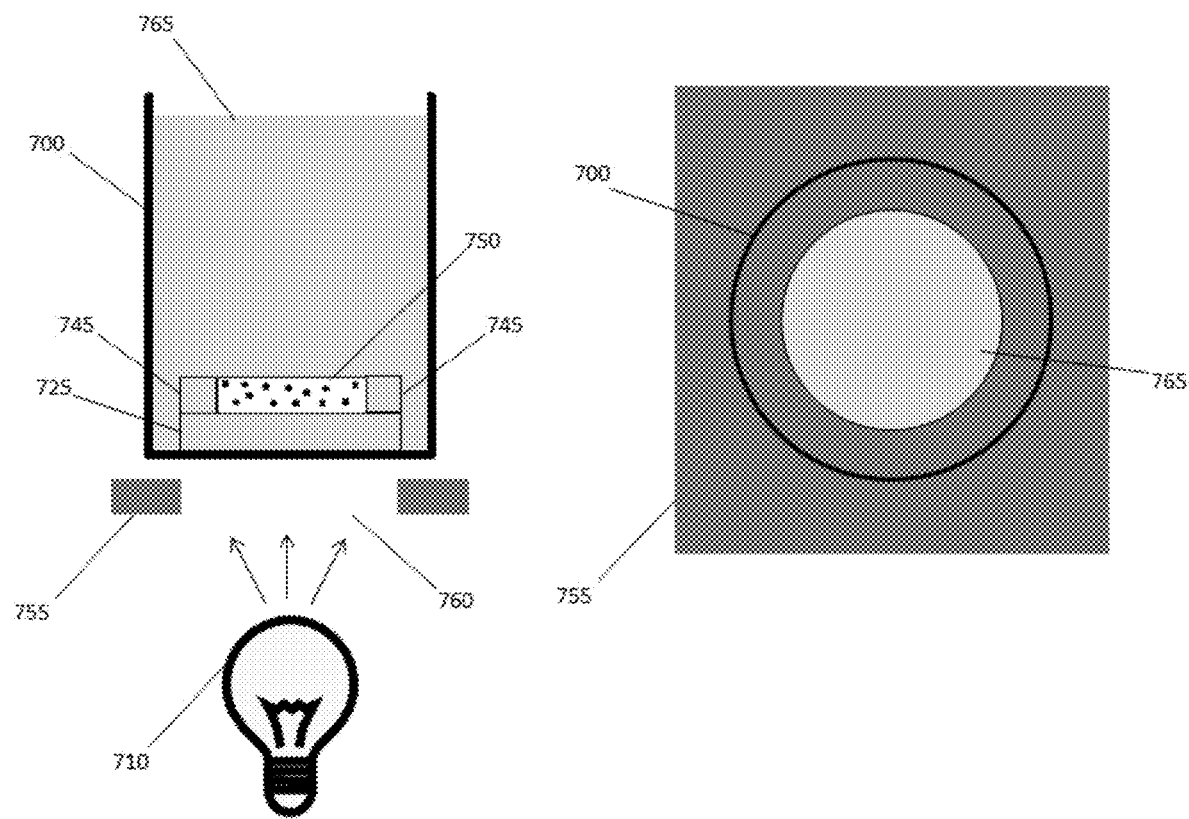
Figure 7J:
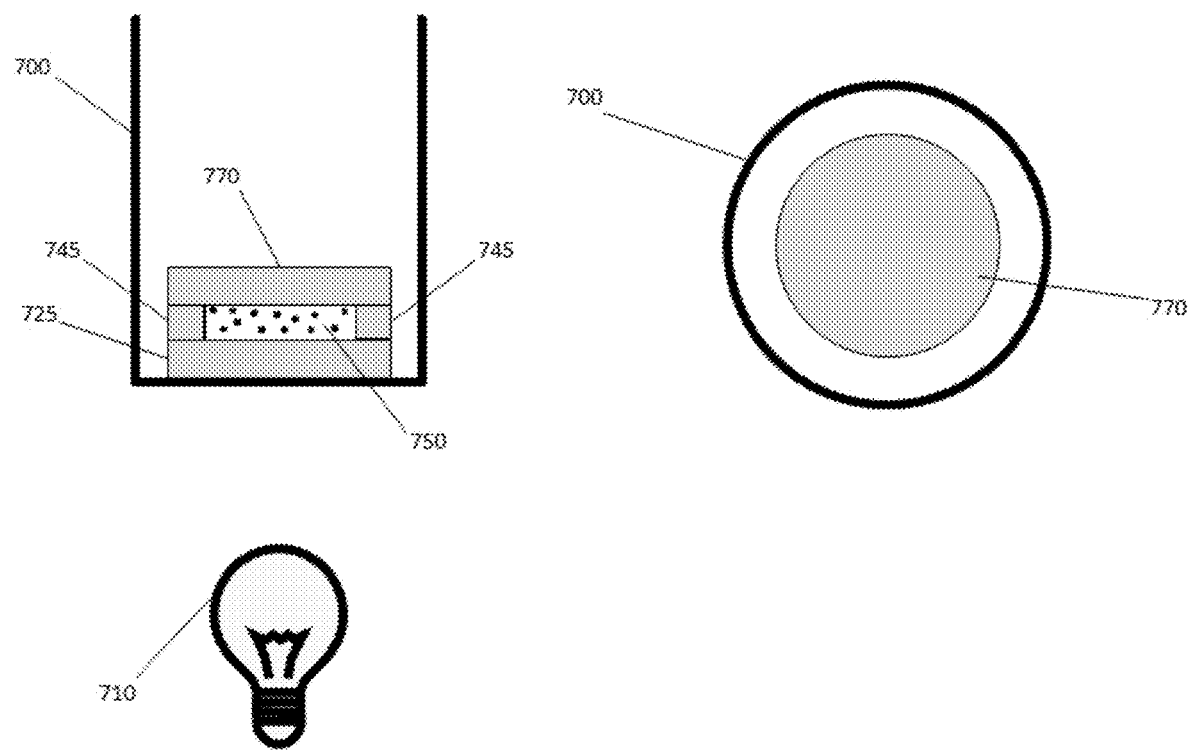

As shown in FIG. 7H, a third light blocking mask 755 with a circular aperture 760 can be interposed between the light source 710 and the well. If a light blocking mask with transient apertures is used this can be achieved by changing the configuration of the aperture, for example by using a controller as described above. This third mask can be identical to or the same mask as shown in FIG. 7A, and similarly positioned essentially concentric with the well 700 and the intermediate hydrogel form. FIG. 7I shows a third photopolymerizable hydrogel precursor 765 instilled into the well 700, which is in turn illuminated by powering the light source 710 to provide light through the aperture 760. The third photopolymerizable hydrogel precursor can be selected to have a density and/or viscosity that is less than that of the cell suspension 750, in order to avoid mixing. As shown in FIG. 7J (which shows the well 700 after illumination and rinsing/washing to remove unreacted third photopolymerizable hydrogel precursor), such illumination is continued for a period of time sufficient to generate a cylindrical hydrogel form 770 coupled to the exposed upper surface of the open cylinder hydrogel form 745, which is in turn coupled to the cylindrical hydrogel form 725. This forms an interior void that encapsulated or encloses the cell suspension 750, which is surrounded by a hydrogel boundary.

Although FIGS. 7A to 7J depict generation of a relatively simple enclosure, it should be appreciated that more complex geometries (for example, extension of the encapsulating portion on an extended stalk, formation of two or more encapsulating regions, etc.) can also be accomplished by suitable selection of light blocking masks and the order in which they are applied.

The inventor contemplates that such methods can be included with an instrument that includes a light source, a holder for a plate that includes one or more test wells, and a guide or channel for placing and securing one or more light blocking masks. If a light blocking mask with transient apertures is used such a device can include a controller that is in electronic communication with the apertures, and that includes a database of aperture configurations and a user interface that permits a user to select one or more configurations. Such and instrument can be provided with a database of such methods that is accessible through a user interface, which can also provide functions such as illumination control, timing, verification of light blocking mask identity, warnings (e.g. improper mask placement, plate misalignment, light source failure, etc.). In some embodiments such a device can be partially or fully automated, for example by the inclusion of appropriate supporting subsystems such as reagent storage, reagent dispensing, plate handling, and/or photomask handling subsystems. Such an instrument can also include a controller for such subsystems.

In some embodiments a series of light blocking masks is provided as a set. In use, members of such a set can be selected and positioned in the printing device sequentially in order to construct the desired three dimensional structure within the well of the microwell plate. In other embodiments two or more light blocking masks can be positioned in the printing device at the same time during illumination. These can be left in place throughout the illumination in order to provide a composite aperture shape and/or conformation that is not present in individual light blocking masks. Alternatively, individual light blocking masks can be selectively removed during the illumination in order to irradiate different portions of the well at different times.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A light blocking mask assembly, comprising:
   a body configured to conform to a lower surface of a microwell plate, and comprising a light blocking portion and a plurality of transmissive apertures having a first spatial arrangement, wherein the plurality of transmissive apertures are transient apertures, a microwell plate
   wherein the microwell plate comprises a plurality of wells having a second spatial arrangement, wherein the first spatial arrangement conforms with the second spatial arrangement.

2. The light blocking mask of claim 1, wherein at least one of the plurality of apertures comprises a liquid crystal panel and a polarizing filter, and wherein the liquid crystal panel is in electronic communication with a controller.

3. The light blocking mask of claim 1, wherein the body comprises a plate holder, wherein the plate holder is configured to contact and stabilize the microwell plate relative to the light blocking mask.

4. The light blocking mask of claim 3, wherein the plate holder comprises a stabilizing body that applies force to a surface of the microwell plate.

5. The light blocking mask of claim 3, wherein the plate holder comprises a recess dimensioned to receive a portion of the microwell plate.

\* \* \* \* \*